United States Patent [19]

Sakakibara et al.

[11] 4,176,009

[45] Nov. 27, 1979

[54] METHOD OF MEASURING COLLAGENASE ACTIVITY

[75] Inventors: Shumpei Sakakibara, Suita; Yutaka Nagai, Koshigaya; Kenji Fujiwara; Takahiro Sakai, both of Tokyo, all of Japan

[73] Assignee: Ajinomoto Co., Inc., Tokyo, Japan

[21] Appl. No.: 853,302

[22] Filed: Nov. 21, 1977

Related U.S. Application Data

[62] Division of Ser. No. 761,020, Jan. 21, 1977, Pat. No. 4,138,394.

[30] Foreign Application Priority Data

Jan. 24, 1976 [JP] Japan .................................. 51/6926
Aug. 30, 1976 [JP] Japan ............................... 51/103505
Aug. 30, 1976 [JP] Japan ............................... 51/103506

[51] Int. Cl.$^2$ ........................................... G01N 31/14
[52] U.S. Cl. ..................................................... 435/24
[58] Field of Search ................................. 195/103.5 R

[56] References Cited

U.S. PATENT DOCUMENTS

| 4,016,042 | 4/1977 | Svendsen | 195/103.5 R |
| 4,028,318 | 6/1977 | Aurell et al. | 195/103.5 R |
| 4,070,245 | 1/1978 | Svendsen | 195/103.5 R |
| 4,119,620 | 10/1978 | Nagatsu et al. | 195/103.5 R |

OTHER PUBLICATIONS

Appel, "Collagenases", *Methods of Enzymatic Analysis*, Bergmeyer (Ed.), (1974), vol. 2, Academic Press, Inc., New York, pp. 1058–1063.

*Primary Examiner*—Raymond N. Jones
*Assistant Examiner*—Esther M. Kepplinger
*Attorney, Agent, or Firm*—Thomas E. Spath; John Boustead

[57] ABSTRACT

A method of measuring collagenase activity using as substrates peptide derivatives having the structure A-Pro-B-Gly-C-Ala-Gly-E wherein A is a hydrophobic neutral or acidic chromophore, B is an amino acid residue, C is Ile or Leu, E is Gln-D-Arg-OH or D-Arg-OH and all the amino acid residues except for Gly are L-configuration unless otherwise stated.

9 Claims, No Drawings

METHOD OF MEASURING COLLAGENASE ACTIVITY

This application is a division copending application, Ser. No. 761,020, filed Jan. 21, 1977 now U.S. Pat. No. 4,138,394.

This invention relates to novel peptide derivatives, and a method of measuring collagenase activity. More specifically, the invention provides novel peptide derivatives, of which one group is useful as substrates specificity of collagenase, and of which the other group is useful as substrates susceptible to non-specific peptidases, not to collagenase, and a method of measuring collagenase activity by using the peptide derivatives as substrates.

Recently, studies on collagen and collagenase have been widely made, and the collagenase levels have been found to fluctuate in tissues or body fluids depending on the kind of connective tissue diseases, for example, in tissues from patients with various skin diseases such as wound and lupus erythematosus, or with gastric ulcer, corneal ulcer, liver cirrhosis or fibrochondroma; in synovial fluids from patients with rheumatoid arthritis; or in granulocytes from patients with essential hypertension, arteriosclerosis, or diabetes mellitus. The present inventors have also found that the collagenase levels are elevated in sera from patients with some hepatobiliary diseases. Thus, the activity measurement of collagenase provides a very useful diagnostic aid for the above-mentioned diseases and closely related diseases.

The activity measurement of collagenase has been carried out by contacting samples containing collagenase with collagen extracted from animal skin or tendon, and measuring the hydrolysis rate. However, this conventional method has the following disadvantages; (1) Natural collagen has very high molecular weights, and a very wide distribution of molecular weights. Thus, it is very difficult to obtain natural collagen having a constant molecular weight, and the preparation procedure thereof is very much complicated. (2) The characteristics of collagen vary depending on the kind and part of animals to be extracted. (3) It is usually indispensable that samples containing collagenase to be measured are contaminated with $\alpha_2$-macroglobulin which is one of serum proteins. However this $\alpha_2$-macroglobulin prevents the activity measurement of collagenese which comprises using natural collagen as substrate. Therefore, the conventional method is not suitable as an accurate activity measurement of collagenase. In order to overcome the above-mentioned third disadvantage, it was tried to treat the complex of collagenase and inhibitory substances such as $\alpha_2$-macroglobulin to make the activity of collagenase revive. This trial failed because side reactions occurred and the activities obtained varied broadly.

The present inventors have thought that the above disadvantages of the conventional method may be overcome by using synthetic peptides as substrates instead of natural collagen, and have made researches on the specific site of cleavage by collagenase, and the relation between collagen and collagenase. As a result, the present inventors have found novel peptide derivatives which are highly specific to collagenase and not affected by $\alpha_2$-macroglobulin during the activity measurement.

The novel peptide derivatives of this invention are those having the following general formula;

A-Pro-B-Gly-C-Ala-Gly-E in which A is a hydrophobic, and neutral or acidic chromophore, B is an amino acid residue, C is Ile or Leu, E is Gln-D-Arg-OH or D-Arg-OH, and all amino acid residues except for Gly are L-configuration unless otherwise stated.

These peptide derivatives release hydrophobic tripeptide derivatives having the sequence of A-Pro-B-Gly-OH by the action of collagenase. Because these tripeptide derivatives are hydrophobic and have chromophores therein, these tripeptide derivatives are easily extracted with suitable organic solvents such as ether, ethyl acetate and n-butanol, and assayed accurately only by subjecting the extract to colorimetry.

Furthermore, it has been found that the present novel peptide derivatives fulfill other general various characteristics required of a substrate; for example, hydrolysis rate, stability, and linear relationship between the amount of hydrolyzed substrate and that of the enzyme, and between the amount of hydrolyzed substrate and the incubation time. As the method of this invention comprises using peptide derivatives as substrates, and extracting and assaying colorimetrically the released tripeptide derivatives, the substrates are specifically required to have a fairly good solubility, and to be easily and sufficiently extracted with organic solvents which hardly extract other substances present in samples having the similar absorption to the tripeptide derivatives, preferably with ethyl acetate. The peptide derivatives of this invention also fulfill the above-mentioned specific requirements sufficiently. Thus, according to the invention, there is provided a very excellent method of measuring collagenase activity.

The chromophore bounded to the amino group of the N-terminal amino acid residue (Pro) includes any hydrophobic, and neutral or acidic chromophores, for example 2,4-dinitrophenyl, 5-dimethyl-amino-1-naphthalenesulfonyl, p-phenylazobenzyloxycarbonyl, p-nitrobenzyloxycarbonyl, p-(4-hydroxy-1-naphthylazo)-benzenesulfonyl and p-phenylazobenzoyl. Of these chromophores, 2,4-dinitrophenyl is most favorably used in terms of handling.

As a result of investigation on characteristics of many kinds of peptide derivatives synthesized by the inventors, the portion B of the general formula hardly affects the so-called substrate specificity (namely the specificity to collagenase), and includes any amino acid residues. The amino acid of the portion B is usually selected from $\alpha$-amino acids having up to 15 carbon atoms and which are present in protein, for example, glycine, alanine, valine, leucine, serine, threonine, proline, phenylalanine, tyrosine, tryptophane, lysine, arginine, aspartic acid, asparagine, glutamic acid, and glutamine. However, the portion B effects the solubilities of the substrates, and the extraction of the released tripeptide derivatives. From this point of view, neutral amino acid residues, especially alanine, proline, leucine and glutamine residues are preferable. Of these preferable amino residues, residues of alanine, leucine and glutamine are most successfully employed. The portion C of the general formula is leucine or isoleucine residue, and both the residues give almost the same properties to the peptide derivatives but the peptide derivative bearing isoleucine residue as the portion C is preferable in terms of specificity to collagenase. Meanwhile, the portion E of the general formula is the residue of D-arginine or glutamyl-D-arginine, and both the residues also give almost the same properties to the peptide derivatives, but the peptide derivatives bearing the residue of glutamyl-D-arginine is more excellent in terms of specificity to collagenase. The peptide derivatives bearing leucine residue as the portion C or D-arginine residue as the portion E are hydrolyzed at a good rate by collagenase, and are thus especially useful as substrates for rapid measurement of collagenase activity.

Among the peptide derivatives of this invention, the best substrates are those bearing 2,4-dinitrophenyl as the portion A, alanine, leucine, proline or glutamine residue, especially alanine, leucine or glutamine residue as the portion B, isoleucine residue as the portion C, and the residue of glutamyl-D-arginine as the portion E, from all the points of view.

The present novel dipeptide derivatives are easily synthesized by methods known in peptide chemistry. Namely, they may be obtained by eliminating the masking groups from the compounds having the formulas:

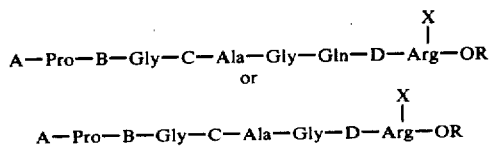

where X is a masking group for the guanidino group of the arginine residue, and R is a masking group for the carboxyl group of the arginine residue. (The formulas include the case where the amino acid residue of the portion B has a side functional group masked with a suitable masking group.)

The masking group suitable for the guanidino group may be chosen from the known groups such as tosyl, nitro, benzyloxycarbonyl, p-nitrobenzyoxycarbonyl, 2-(isopropyloxycarbonyl)-3,4,5,6-tetrachlorobenzoyl, especially the former three groups, while the carboxyl group may be masked by converting the same to ester group such as benzyl, t-butyl, p-nitrobenzyl, or p-methoxybenzyl ester group, especially to benzyl or t-butyl ester group.

The masking groups are eliminated by known methods depending on the masking groups and those for side functional groups, if any. It is important to eliminate only the masking groups without affecting other members in this elimination reaction. Hydrogen fluoride treatment is preferable as elimination method, because both the masking groups, X and R, are eliminated at the same time.

Hydrogen fluoride treatment is usually carried out under anhydrous condition and at −70° to 20° C., preferably at −10° to 10°. The treatment proceeds in the presence of solvent or in the absence of it, but is preferably carried out in excess hydrogen fluoride which may function as solvent. The treatment is preferably carried out in the copresence of a small amount of anisol or phenol to prevent side reactions. The isolation of the demasked product may be made in the conventional manner.

The starting masked peptide derivatives may be synthesized by methods known in peptide chemistry, for example stepwise elongation, fragment condensation, and the combination of these methods. If the amino acids corresponding to the portion B have side functional groups, they may be employed after the functional groups are masked in a conventional manner.

These masking groups for the side functional groups are eliminated after, before, or simultaneously with the elimination of the masking groups for the arginine residue, depending on the masking groups for the side functional groups. The chromophore may be introduced to the N-terminal proline at the beginning of peptide synthesis, or to the fragment or final peptide having the N-terminal proline residue of which amino group is masked with conventional amino-masking groups such as t-butyloxycarbonyl, benzyloxycarbonyl, and t-amyloxycarbonyl, by substituting the amino-masking group with the chromophore.

The collagenase activity is measured without difficulty using the peptide derivatives as substrates, as in the case of natural collagen. An aqueous solution of the peptide derivative having a suitable concentration is first prepared. The optimum pH of the substrate solution varies slightly depending on the kind of substrate employed, and is usually in the range of 6 to 9, preferably 7 to 8.

The collagenase activity is measured by contacting the substrate with collagenase or a sample containing the same in an aqueous medium, preferably in a buffer solution such as tris-HCl buffer, at 30° to 45° C., usually at 35° to 40° C. for a certain period, deactivating the collagenase in the usual manner. The incubation time is determined by the amount of substrate and enzyme. The amount of released A-Pro-B-Gly-OH is easily assayed by extracting the same with suitable organic solvent such as ethyl acetate, ether, or n-butanol, and measuring the absorbance of the elute at the wave length suitable for individual chromophore, for example, 365 nm for 2,4-dinitrophenyl, 389 nm for p-(4-hydroxy-1-naphthyazo)-benzenesulfonyl and 325 nm for p-phenylazobenzoyl.

As the peptide derivatives of this invention are highly specific to collagenase, the collagenase activity is accurately measured by using the same as substrates in case of usual samples containing collagenase, such as serum and synovial fluid. However, if samples containing other non-specific peptidases highly, such as samples from tissue of liver or kidney, are employed, it has been found that the substrates are partly hydrolyzed by the other non-specific peptidases and the accuracy of the collagenase activity obtained is not always acceptable. Then, the present inventors have searched other peptide derivatives which are susceptible to non-specific peptidase, not to collagenase, in order to overcome the above disadvantage by using these second peptide derivatives as referential substrates. As a result, they have found that novel peptide derivatives having the structure of the first peptide derivatives lacking the proline residue at the N-terminus (namely, A-B-Gly-C-Ala-Gly-E) fulfill this requirement. These second peptide derivatives are also easily synthesized in the aforementioned manner.

In the activity measurement, these second peptide derivatives are used as the referential substrates to the first peptide derivatives. Namely, these second peptide derivatives are contacted with samples containing collagenase and non-specific peptidases, the peptide fragments containing the chromophore are extracted and the absorbance of the extract is measured, under the same conditions as in the case of the first peptide derivatives. The more accurate collagenase activity is thus calculated without the affection of non-specific peptidases by subtracting the absorbance obtained by using the second peptide derivatives as substrates from that obtained by using the first peptide derivatives.

The following Examples illustrate the present invention in more detail. In Examples, the following abbreviations are used;

| BOC | : t-butyloxycarbonyl, | Z | : benzyloxycarbonyl, |
|---|---|---|---|
| DNP | : 2,4-dinitrophenyl, | NABS | : p-(4-hydroxy-1-naphthylazo)-benzenesulfonyl, |
| PAB | : p-phenylazobenzoyl, | —OBzl | : benzyl ester, |
| —OEt | : ethyl ester, | —OSu | : N-hydroxysuccinimido ester, |
| WSCI | : 1-ethyl-3-(3-dimethylaminopropyl)-carbodiimide | | |
| DMF | : dimethylformamide, | THF | : tetrahydrofuran |
| TosOH | : p-toluenesulfonic acid | | |

Purified collagenase used in Examples was prepared from cultured media of tadpole skin explants as described in Biochem. Biophs. Acta, 263 564(1972), and non-specific peptidases were prepared by subjecting 5 ml of fresh adult human serum to chromatography on a calibrated Sephadex G-200 superfine gel column equilibrated with 0.05 M Tris-HCl buffer, pH 7.5, containing 0.15 M NaCl and 5 mM $CaCl_2$, and gathering the effluent fractions corresponding to molecular weights of 100,000–180,000.

EXAMPLE 1

(DNP-Pro-Gln-Gly-Ile-Ala-Gly-Gln-D-Arg-OH)

(1) D-Arg($NO_2$)TOBzl. 2 TosOH

D-Arg($NO_2$) (16.4 g, 0.075 mol),p-toluenesulfonic acid (31.4 g, 0.165 mol), and benzylalcohol (37 ml) were suspended in chloroform (150 ml), and the suspension was refluxed for 5 hours to a clear solution.

The solution was, after added with toluene (100 ml), distilled under reduced pressure, and chloroform (150 ml) was added to the residue, which was refluxed again for 5 hours. The resulting solution was added with toluene (100 ml×2), distilled under reduced pressure, and the residue was solidified by the addition of dry ether. The solid obtained was filtered out, washed with dry ether, and recrystallized from methanol-dry ether. The crystals were dried over phosphorus pentoxide for 12 hours.

Yield 42 g (86%)
m.p. 132°–135° C.
$[\alpha]_D^{20}$ −12.0° (C=3, pyridine)

(2) Boc-Gln-D-Arg($NO_2$)-OBz

Boc-Gln (5.0 g, 20 m mol) and D-Arg($NO_2$,-OBzl. 2 TosOH (13.1 g, 20 m mol) were suspended in DMF-THF (5 ml-20 ml), and triethylamine (2.8 ml, 20 m mol), 1-hydroxybenztriazol (2.7 g, 20 m mol), and WSCI (3.6 ml, 20 m mol) were added to the suspension at −10° C. The reaction mixture was stirred at −10° C. for 1 hour, and then at room temperature for 16 hours.

The THF of the reaction mixture was evaporated under reduced pressure, and the resulting mixture was dissolved in chloroform (300 ml), which solution was washed successively with 1 N-hydrochloric acid (100 ml×3), water (100 ml), 10% sodium carbonate solution (100 ml×3) and water (100 ml×2). The chloroform of the washed mixture was evaporated under reduced pressure, and the residue was crystallized by the addition of ether. The crystals were filtered out, washed with water and ether, recrystallized from methanol-ether, and dried, over phosphorus pentoxide for 12 hours.

Yield 8.5 g (78%)
m.p. 147°–154° C. (decomp.)
$[\alpha]_D^{20}$ +5.3° (C=1, DMF)
Elemental Analysis

|  | C | H | N % |
|---|---|---|---|
| Calcd. for $C_{23}H_{35}O_8N_7 \cdot \frac{1}{2}H_2O$ | 50.54 | 6.64 | 17.94 |
| Found | 50.67 | 6.56 | 17.91 |

(3) BOC-Ile-Ala-Gly-OEt

25% Hydrogen bromide solution in acetic acid (50 ml) was added with cooling to Z-Ala-Gly-OEt (12.4 g, 40 m mol), and the resulting solution was stirred at room temperature for 1 hour.

Ether was added to the solution to yield precipitates, which were washed with ether, and dried over sodium hydroxide. The obtained solid was dissolved in DMF (30 ml), and the resulting solution was adjusted to pH 7–7.5 with triethylamine, added with BOC-Ile-OSu (14.4 g, 44 m mol) and stirred at room temperature for 24 hours.

Water (200 ml) was added to the reaction mixture, and the resulting solution was extracted three times with ethyl acetate (200 ml, 150 ml, 100 ml). The organic layer obtained was washed successively with 1 N-hydrochloric acid, water, 5% sodium hydrogencarbonate solution, and dried over anhydrous magnesium sulfate. The solvent was evaporated under reduced pressure, and the residue was crystallized by the addition of ether, recrystallized from ethyl acetate-ether, and dried over phosphorus pentoxide at room temperature for 12 hours.

Yield 13.0 g (84%)
m.p. 148.5°–149° C.
$[\alpha]_D^{21}$ −50.9° (C=2.2, ethanol)
Elemental Analysis

|  | C | H | N % |
|---|---|---|---|
| Calcd. for $C_{18}H_{33}O_6N_3$ | 55.79 | 8.58 | 10.85 |
| Found | 55.54 | 8.74 | 10.80 |

(4) Boc-Ile-Ala-Gly-OH

Boc-Ile-Ala-Gly-OEt (3.9 g, 10 m mol) was dissolved in dioxane (20 ml), and 1 N-sodium hydroxide solution (11 ml, 11 m mol) was added dropwise to the solution with stirring and cooling. The resulting solution was further stirred for 1 hour, and neutralized with 1 N-hydrochloric acid, and the solvent was evaporated under reduced pressure. The water layer obtained was adjusted to pH 2 with 1 N-hydrochloric acid, and extracted twice with ethyl acetate (100 ml, 50 ml). The separated organic layer was washed with saturated sodium chloride solution, and dried over anhydrous sodium sulfate. The solvent of the dried solution was evaporated under reduced pressure, and the residue was crystallized by the addition of ether. The crystals were filtered out, recrystallized from ethyl acetate-ether, and dried over phosphorus pentoxide at room temperature for 12 hours.

Yield 3.0 g (84%)
m.p. 156°–158° C.
$[\alpha]_D^{21}$ −42.3° (C=1.6, ethanol)
Elemental Analysis

| | C | H | N % |
|---|---|---|---|
| Calcd. for $C_{16}H_{29}O_6N_3 \cdot \frac{1}{2}H_2O$ | 52.15 | 8.21 | 11.40 |
| Found | 52.06 | 8.14 | 11.52 |

(5) Boc-Ile-Ala-Gly-Gln-D-Arg(NO₂)-OBzl

Boc-Gln-D-Arg(NO₂)-OBzl (5.5 g, 10 m mol) was added to trifluoroacetic acid (20 ml) with cooling, and the resulting solution was stirred for 5 minutes with cooling, and furthermore stirred for 45 minutes at room temperature. 6 N-Hydrochloric acid in dioxane (1.7 ml, 10 m mol) was added to the reaction mixture, and excess trifluoroacetic acid was evaporated under reduced pressure. The residue was solidified by the addition of ether, washed with ether, and dried over sodium hydroxide under reduced pressure.

The solid obtained was dissolved in DMF-THF (10 ml-30 ml), and the solution was adjusted to pH 5 with N-methylmorpholine at −10° C. Boc-Ile-Ala-Gly-OH (3.6 g, 10 m mol), 1-hydroxybenzotriazol (2 g, 15 m mol) and WSCI (2.7 ml, 15 m mol) were successively added to the above mixture, which was stirred at −10° C. for 1 hour, and furthermore stirred at room temperature for 16 hours. The solvent was evaporated under reduced pressure, and 1 N-hydrochloric acid (100 ml) was added to the residue. The precipitated solid was filtered out, washed with water, 5% sodium hydrogencarbonate, and suspended in DMF-methanol with warming. Ethyl acetate was added to the suspension, and the precipitated solid was filtered out, and dried over phosphoryl pentoxide for 12 hours.

Yield 6.8 g (86%)

m.p. 217°–221° C. (decomp.)

$[\alpha]_D^{20}$ +7.7° (C=0.3, hexamethylphosphoryltriamide)

Elemental Analysis

| | C | H | N % |
|---|---|---|---|
| Calcd. for $C_{34}H_{54}O_{11}N_{10} \cdot \frac{1}{2}H_2O$ | 51.83 | 7.04 | 17.78 |
| Found | 51.68 | 6.98 | 17.73 |

(6) DNP-Pro-Gln-Gly-OH

H-Pro-Gln-Gly-OH (2.7 g, 9 m mol) was dissolved in 5% sodium hydrogencarbonate solution (50 ml) with ice-cooling, and dinitrofluorobenzene in acetone (2.4 g, 13 m mol; 20 ml) was added to the solution. The reaction mixture was stirred for 1 hour with ice-cooling, and further stirred at room temperature overnight.

The solvent was evaporated under reduced pressure, adjusted to pH 2 with 6 N-hydrochloric acid, and diluted with water (200 ml). The solution was passed through a column of a high porous resin (Diaion HP-20), which was washed with water, and eluted with methanol. The methanol solution obtained was concentrated under reduced pressure, and ether was added to the residue. The precipitated solid was filtered out, resolidified from methanol-ether and dried over phosphorous pentoxide for 12 hours.

Yield 3.0 g (71%)

m.p. 205°–207° C. (decomp.)

$[\alpha]_D^{20}$ −292.4° (C=1.0, DMF)

Elemental Analysis

| | C | H | N % |
|---|---|---|---|
| Calcd. for $C_{18}H_{22}O_9N_6$ | 46.35 | 4.75 | 18.02 |
| Found | 46.20 | 4.94 | 18.13 |

(7) DNP-Pro-Gln-Gly-Ile-Ala-Gly-Gln-D-Arg(NO₂)-OBzl

Boc-Ile-Ala-Gly-Gln-D-Arg(NO₂)-OBzl (1 g, 1.3 m mol) was added to trifluoroacetic acid (5 ml) with cooling, and the solution was stirred for 10 minutes with cooling, and furthermore stirred for 50 minutes at room temperature. 6 N-Hydrochloric acid in dioxane (0.5 ml, 3 m mol) was added to the reaction mixture, and the excess trifluoroacetic acid was evaporated under reduced pressure. The residue was solidified by the addition of ether, washed with ether, and dried over sodium hydroxide.

The solid obtained was dissolved in DMF (20 ml), and DNP-Pro-Gln-Gly-OH (0.6 g, 1.3 m mol), 1-hydroxybenzotriazol (2.10 mg, 1.6 m mol) and WSCI (0.29 ml, 1.6 m mol) were successively added thereto at −10° C. The reaction mixture was stirred at −10° C. for 1 hour, and further stirred at room temperature overnight, and added with 1 N-hydrochloric acid to yield precipitates. The precipitates were filtered out, and dried over phosphorous pentoxide for 12 hours at room temperature.

Yield 1.3 g (89%)

m.p. 247°–250° C. (decomp.)

$[\alpha]_D^{20}$ −68.3° (C=0.5, hexamethylphosphoryltriamide)

Elemental Analysis

| | C | H | N % |
|---|---|---|---|
| Calcd. for $C_{47}H_{66}O_{17}N_{16}$ | 50.08 | 5.90 | 19.88 |
| Found | 50.08 | 6.12 | 19.52 |

(8) DNP-Pro-Gln-Gly-Ile-Ala-Gly-Gln-D-Arg-OH

DNP-Pro-Gln-Gly-Ile-Ala-Gly-Gln-D-Arg(NO₂)-OBzl (1.3 g, 1.2 m mol) was dissolved in anhydrous hydrogen fluoride (30 ml) in the presence of anisol (2 ml), and the solution was stirred at 0° C. for 1 hour. After removal of the excess hydrogen fluoride by evaporation under reduced pressure, the residue was solidified by the addition of ether.

The solid was washed with ether, and dissolved in acetic acid, and the solution was passed through a column of a strong-base anion exchange resin (Dowex 1×2, Acetate form). After removal of the acetic acid from the effluent by evaporation, the residue was solidified with ether. The solid was filtered out, resolidified from acetic acid-ether, and dried over phosphorous pentoxide for 24 hours at room temperature.

Yield 1.0 g (81%)

m.p. 230°–233.5° C. (decomp.)

$[\alpha]_D^{20}$ −233.2° C. (C=0.6, 50% acetic acid)

Elemental Analysis

| | C | H | N % |
|---|---|---|---|
| Calcd. for $C_{40}H_{41}O_{15}N_{15} \cdot CH_3COOH \cdot H_2O$ | 47.14 | 6.31 | 19.64 |
| Found | 46.90 | 6.64 | 19.40 |

EXAMPLE 2

(NABS-Pro-Gln-Gly-Ile-Ala-Gly-Gln-D-Arg-OH)

(1) Boc-Gln-Gly-OBzl

Gly-OBzl.TosOH (18.5 g, 55 m mol) was neutralized and coupled with Boc-Gln (12.3 g, 50 m mol) in the manner similar to that of Example 1, paragraph 2).

Yield 15.7 g (80%)
m.p. 126°–127° C.
$[\alpha]_D^{20}$ −9.6° (C=1, DMF)

(2) Boc-Pro-Gln-Gly-OBzl

Boc-Gln-Gly-OBzl (11.8 g, 0.03 mol) was demasked with respect to the N-masking group and coupled with Boc-Pro-OH (6.5 g, 0.03 mol) in the manner similar to that of Example 1, paragraph 5).

Yield 8.0 g (54%)
m.p. 152°–154° C.
$[\alpha]_D^{28}$ −41.1° (C=0.5, DMF)
Elemental Analysis

|  | C | H | N % |
| --- | --- | --- | --- |
| Calcd. for $C_{24}H_{14}O_7N_4 \cdot \frac{1}{2}H_2O$ | 58.22 | 7.02 | 11.32 |
| Found | 58.14 | 6.73 | 11.30 |

(3) Boc-Pro-Gln-Gly-OH

Boc-Pro-Gln-Gly-OBzl (4.0 g, 8.2 m mol) was dissolved in 90% methanol (60 ml), and hydrogen gas was passed through the solution in the presence of a spoonful of Pd-C for 6 hours. After removing the catalyst by filtration, the filtrate was concentrated under reduced pressure, and the residue was solidified by the addition of ether and recrystallized from methanol-ether.

Yield 2.9 g (91%)

(4) Boc-Pro-Gln-Gly-Ile-Ala-Gly-Gln-D-Arg(NO$_2$)-OBzl

Boc-Ile-Ala-Gly-Gln-D-Arg(NO$_2$)-OBzl (1,2 g, 1.5 m mol) was demasked with respect to the N-masking group, and coupled with Boc-Pro-Gln-Gly-OH (0.6 g, 1.5 m mol) in the manner similar to that of Example 1, paragraph 5).

Yield 1.1 g (69%)
m.p. 224°–229° C. (decomp.)
$[\alpha]_D^{28}$ −6.8°(C=0.3, DMF)
Elemental Analysis

|  | C | H | N % |
| --- | --- | --- | --- |
| Calcd. for $C_{46}H_{72}O_{15}N_{14} \cdot 3/2N_2O$ | 50.76 | 6.95 | 18.02 |
| Found | 50.55 | 6.55 | 17.85 |

(5) NABS-Pro-Gln-Gly-Ile-Ala-Gly-Gln-D-Arg-OH

Boc-Pro-Gln-Gly-Ile-Ala-Gly-Gln-D-Arg(NO$_2$)-OBzl (300 mg, 0.28 m mol) was treated with hydrogen fluoride (7 ml) in the presence of anisol (0.5 ml) at 0° C. for 1 hour. The reaction mixture was worked up as in Example 1, paragraph 8) to yield the residue containing H-Pro-Gln-Gly-Ile-Ala-Gly-Gln-D-Arg-OH.

The residue was dissolved in 5 ml water, and thereto were sodium hydrogencarbonate (110 mg, 1.3 m mol) and p-(4-hydroxy-1-naphthylazo)benzenesulfonylchloride (240 mg, 0.7 m mol) in THF (5 ml) added with cooling. The reaction mixture was stirred at room temperature for 3 hours. After removal of the THF by evaporation under reduced pressure, the reaction mixture was extracted with ethyl acetate. The remaining water layer was diluted with a large amount of water, and passed through a column of a high porous resin (Diaion HP-20), which was washed with water, and eluted with 90% methanol.

The elute was dried up, and the residue was dissolved in 50% acetic acid and passed through a column of a strong-base anion-exchange resin (Dowex 1×2, Acetate form), which was eluted with 50% acetic acid.

Yield 190 mg (57%)
m.p. 230°–239° C. (decomp.)
$[\alpha]_D^{28}$ −84.2° (C=0.5, 50% acetic acid)
Elemental Analysis

|  | C | H | N % |
| --- | --- | --- | --- |
| Calcd. for $C_{50}H_{69}O_{14}N_{15}S \cdot CH_3COOH \cdot H_2O$ | 49.24 | 6.44 | 16.57 |
| Found | 49.11 | 6.34 | 16.77 |

H

EXAMPLE 3

(PAB-Pro-Gln-Gly-Ile-Ala-Gly-Gln-D-Arg-OH)

(1) PAB-Pro-Gln-Gly-OH

H-Pro-Gln-Gly-OH (400 mg, 1.3 m mol) was dissolved in water (5 ml), and thereto were sodium hydrogencarbonate (220 mg, 2.6 m mol) and p-phenylazobenzoylchloride (320 mg, 1.3 m mol) in THF (5 ml) added with cooling. The reaction mixture was stirred at room temperature for 3 hours. The THF of the mixture was evaporated under reduced pressure, and the resulting aqueous solution was adjusted to pH2 with 1 N-hydrochloric acid, and extracted with ethyl acetate. The ethyl acetate layer was washed with a saturated sodium chloride solution, dried with anhydrous sodium sulfate, and concentrated to dryness. The residue was resolidified from methanol-ether.

Yield 360 mg (53%)
m.p. 189°–194° C. (decomp.)
$[\alpha]_D^{28}$ −2.0° (C=0.5, DMF)
Elemental Analysis

|  | C | H | N % |
| --- | --- | --- | --- |
| Calcd. for $C_{25}H_{28}O_6N_6 \cdot 7/4H_2O$ | 55.60 | 5.88 | 15.56 |
| Found | 55.61 | 5.48 | 15.33 |

(2) PAB-Pro-Gln-Gly-Ile-Ala-Gly-Gln-D-Arg(NO$_2$)-OBzl

Boc-Ile-Ala-Gly-Gln-D-Arg(NO$_2$)-OBzl (200 mg, 0.26 m mol) was demasked with respect to the N-masking group, and coupled with PAB-Pro-Gln-Gly-OH (130 mg, 0.26 m mol) as in Example 1, paragraph 5)

Yield 230 mg (75%)

(3) PAB-Pro-Gln-Gly-Ile-Ala-Gly-Gln-D-Arg-OH

PAB-Pro-Gln-Gly-Ile-Ala-Gly-Gln-D-Arg(NO$_2$)-OBzl (200 mg. 0.17 m mol) was treated with hydrogen fluoride in the manner similar to that of Example 1, paragraph 8).

Yield 150 mg (80%)
m.p. 196°–205° C. (decomp.)
$[\alpha]_D^{28}$ +34.9° (C=0.4, 50% acetic acid)

EXAMPLE 4

(DNP-Pro-Gln-Gly-Leu-Ala-Gly-Gln-D-Arg-OH)

(1) Boc-Leu-Ala-Gly-OEt

Z-Ala-Gly-OEt (6.2 g, 0.02 mol) was demasked and coupled with Boc-Leu-OSu (6.6 g, 0.02 mol) in the manner similar to that of Example 1, paragraph 3).

Yield 4.7 g (61%)

m.p. 139°-142° C.
$[\alpha]_D^{28}$ −21.6° (C=0.8, DMF)
Elemental Analysis

|  | C | H | N % |
|---|---|---|---|
| Calcd. for $C_{18}H_{33}O_6N_3$ | 55.79 | 8.58 | 10.85 |
| Found | 55.41 | 8.73 | 11.01 |

(2) Boc-Leu-Ala-Gly-OH
Boc-Leu-Ala-Gly-OEt (4.5 g, 0.012 mol) was dissolved in methanol (20 ml), and treated with sodium hydroxide in the manner similar to that of Example 1, paragraph 4).
Yield 4.0 g (92%)
(3) Boc-Leu-Ala-Gly-Gln-D-Arg(NO₂)-OBzl
Boc-Gln-D-Arg(NO₂)-OBzl (2.0 g, 3.7 m mol) was demasked with respect to the N-masking group and coupled with Boc-Leu-Ala-Gly-OH (1.3 g, 3.7 m mol) in the manner similar to that of Example 1, paragraph 5).
Yield 2.0 g (70%)
m.p. 213°-218° C. (decomp.)
$[\alpha]_D^{28}$ +0.5° (C=0.4, DMF)
Elemental Analysis

|  | C | H | N % |
|---|---|---|---|
| Calcd. for $C_{34}H_{54}O_{11}N_{10} \cdot N_2O$ | 51.24 | 7.08 | 17.58 |
| Found | 51.25 | 6.91 | 17.80 |

(4) DNP-Pro-Gln-Gly-Leu-Ala-Gly-Gln-D-Arg(NO₂)-OBzl
Boc-Leu-Ala-Gly-Gln-D-Arg(NO₂)-OBzl (350 mg, 0.45 m mol) was demasked with respect to the N-masking group and coupled with DNP-Pro-Gln-Gly-OH (210 mg, 0.45 m mol) in the manner similar to that of Example 1, paragraph 7).
Yield 450 mg (89%)
(5) DNP-Pro-Gln-Gly-Leu-Ala-Gly-Gln-D-Arg-OH
DNP-Pro-Gln-Gly-Leu-Ala-Gly-Gln-D-Arg(NO₂)-OBzl (300 mg, 0.27 m mol) was treated with hydrogen fluoride in the manner similar to that of Example 1, paragraph 8).
Yield 250 mg (85%)
m.p. 221°-226° C. (decomp.)
$[\alpha]_D^{28}$ −256.5° (C=0.5, 50% acetic acid)
Elemental Analysis

|  | C | H | N % |
|---|---|---|---|
| Calcd. for $C_{40}H_{61}O_{15}N_{15} \cdot 2CH_3COOH \cdot 3.5H_2O$ | 44.97 | 6.52 | 17.88 |
| Found | 45.21 | 6.24 | 17.62 |

EXAMPLE 5

(DNP-Pro-Ala-Gly-Ile-Ala-Gly-Gln-D-Arg-OH)

(1) DNP-Pro-Ala-Gly-OH
H-Pro-Ala-Gly-OH (630 mg, 2.6 m mol) was reacted with dinitrofluorobenzene (600 mg, 3.1 m mol) in the manner similar to that of Example 1, paragraph 6).
Yield 710 mg (67%)
m.p. 187°-190° C. (decomp.)
$[\alpha]_D^{28}$ −423.1° (C=0.4, DMF)
(2) DNP-Pro-Ala-Gly-Ile-Ala-Gly-Gln-D-Arg(NO₂)-OBzl
Boc-Ile-Ala-Gly-Gln-D-Arg(NO₂)-OBzl (480 mg, 0.61 m mol) was demasked with respect to the N-masking group and coupled with DNP-Pro-Ala-Gly-OH (250 mg, 0.61 m mol) in the manner similar to that of Example 1, paragraph 7).
Yield 540 mg (83%)
(3) DNP-Pro-Ala-Gly-Ile-Ala-Gly-Gln-D-Arg-OH
DNP-Pro-Ala-Gly-Ile-Ala-Gly-Gln-D-Arg(NO₂)-OBzl (270 mg, 0.25 m mol) was treated with hydrogen trifluoride in the manner similar to that of Example 1, paragraph 8).
Yield 220 mg (88%)
m.p. 228°-235° C. (decomp.)
$[\alpha]_D^{28}$ −287.5° (C=0.5, 50% acetic acid)
Elemental Analysis

|  | C | H | N % |
|---|---|---|---|
| Calcd. for $C_{38}H_{58}O_{14}N_{14} \cdot 7/2H_2O$ | 45.73 | 6.56 | 19.65 |
| Found | 46.03 | 6.25 | 19.48 |

EXAMPLE 6

(DNP-Pro-Ala-Gly-Leu-Ala-Gly-Gln-D-Arg-OH)

(1) DNP-Pro-Ala-Gly-Gln-D-Arg(NO₂)-OBzl
Boc-Leu-Ala-Gly-Gln-D-Arg(NO₂)-OBzl 49. mg, 0.63 m mol) was demasked with respect to the N-masking group and coupled with DNP-Pro-Ala-Gly-OH (260 mg, 0.63 m mol) in the manner similar to that of Example 1, paragraph 7).
Yield 590 mg (72%)
(2) DNP-Pro-Ala-Gly-Leu-Ala-Gly-Gln-D-Arg-OH
DNP-Pro-Ala-Gly-Leu-Ala-Gly-Gln-D-Arg(NO₂)-OBzl (250 mg, 0.23 m mol) was treated with hydrogen fluoride in the manner similar to that of Example 1, paragraph 8).
Yield 190 mg (83%)
m.p. 219°-227° C. (decomp.)
$[\alpha]_D^{28}$ −274.7° (C=0.5, 50% acetic acid)
Elemental Analysis

|  | C | H | N % |
|---|---|---|---|
| Calcd. for $C_{36}NH_{58}O_{14}N_{14} \cdot 2CH_3COOH \cdot 5/2H_2O$ | 45.85 | 6.51 | 17.83 |
| Found | 46.04 | 6.23 | 17.61 |

EXAMPLE 7

(DNP-Pro-Pro-Gly-Ile-Ala-Gly-Gln-D-Arg-OH)

(1) DNP-Pro-Pro-Gly-OH
H-Pro-Pro-Gly-OH (670 mg, 2.5 m mol) was reacted with dinitrofluorobenzene (560 mg, 3.0 m mol) in the manner similar to that of Example 6, paragraph 6).
Yield 520 mg (48%)
m.p. 155°-165° C. (decomp.)
$[\alpha]_D^{28}$ −413.0° (C=0.4, DMF)
(2) DNP-Pro-Pro-Gly-Ile-Ala-Gly-Gln-D-Arg(NO₂)-OBzl
Boc-Ile-Ala-Gly-Gln-D-Arg(NO₂)-OBzl (500 mg, 0.64 m mol) was demasked with respect to the N-masking group and coupled with DNP-Pro-Pro-Gly-OH (280 mg, 0.64 m mol) in the manner similar to that of Example 1, paragraph 7).
Yield 510 mg (73%)
(3) DNP-Pro-Pro-Gly-Gln-D-Arg-OH
DNP-Pro-Pro-Gly-Ile-Ala-Gly-Gln-D-Arg(NO₂)-OBzl was treated with hydrogen fluoride in the manner similar to that of Example 1, paragraph 8).

Yield 200 mg (85%)
m.p. 233°-238° C. (decomp.)
$[\alpha]_D^{28}$ −325.2° (C=0.5, 50% acetic acid)
Elemental Analysis

|  | C | H | N % |
|---|---|---|---|
| Calcd. for $C_{40}H_{60}O_{14}N_{14}$ . $2CH_3COOH$ . $3H_2O$ | 46.55 | 6.57 | 17.28 |
| Found | 46.80 | 6.33 | 17.16 |

EXAMPLE 8

(DNP-Pro-Gln-Gly-Ile-Ala-Gly-D-Arg-OH)

(1) Boc-Ile-Ala-Gly-D-Arg($NO_2$)-OBzl

D-Arg($NO_2$)-OBzl.2TosOH (5.3 g, 8.4 m mol) was neutralized and coupled with Boc-Ile-Ala-Gly-OH (3.0 g, 8.4 m mol) in the manner similar to that of Example 1, paragraph 2).

Yield 4.3 g (79%)

(2) DNP-Ile-Ala-Gly-D-Arg($NO_2$)-OBzl

Boc-Ile-Ala-Gly-D-Arg($NO_2$)-OBzl (900 mg, 1.4 m mol) was demasked with respect to the N-masking group, and coupled with DNP-Pro-Gln-Gly-OH (580 mg, 1.4 m mol) in the manner similar to that of Example 1, paragraph 7).

Yield 1.1 g (79%)

(3) DNP-Pro-Gln-Gly-Ile-Ala-Gly-D-Arg-OH

DNP-Pro-Gln-Gly-Ile-Ala-Gly-D-Arg($NO_2$)-OBzl (300 mg, 0.3 m mol) was treated with hydrogen fluoride in the manner similar to that of Example 1, paragraph 8).

Yield 160 mg (59%)
m.p. 230°-234° C. (decomp.)
$[\alpha]_D^{28}$ −258.0° (C=0.5, 50% acetic acid)
Elemental Analysis

|  | C | H | N % |
|---|---|---|---|
| Calcd. for $C_{35}H_{53}O_{13}N_{13}$ . $2CH_3COOH$ . $3/2H_2O$ | 46.32 | 6.38 | 18.01 |
| Found | 46.21 | 6.22 | 18.35 |

EXAMPLE 9

(DNP-Pro-Leu-Gly-Ile-Ala-Gly-Gln-D-Arg-OH)

(1) DNP-Pro-Leu-Gly-Ile-Ala-Gly-Gln-D-Arg($NO_2$)-OBzl

Boc-Ile-Ala-Gly-Gln-D-Arg($NO_2$)-OBzl (1.0 g, 1.3 m mol) was demasked with respect to the N-masking group and coupled with DNP-Pro-Leu-Gly-OH (0.6 g, 1.3 m mol) in the manner similar to that of Example 1, paragraph 7).

Yield 1.35 g (93%)

(2) DNP-Pro-Leu-Gly-Ile-Ala-Gly-Gln-D-Arg-OH

DNP-Pro-Leu-Gly-Ile-Ala-Gly-Gln-D-Arg($NO_2$)-OBzl (1.0 g, 0.9 m mol) was treated with hydrogen fluoride in the manner similar to that of Example 1, paragraph 8).

Yield 0.75 g (79%)
m.p. 238°-246° C. (decomp.)
$[\alpha]_D^{20}$ −272.3° (C=0.6, 50% acetic acid)
Elemental Analysis

|  | C | H | N % |
|---|---|---|---|
| Calcd. for $C_{41}H_{64}O_{14}N_{14}$ . $4H_2O$ | 46.94 | 6.92 | 18.70 |
| Found | 47.12 | 6.74 | 18.80 |

EXAMPLE 10

(DNP-Gln-Gly-Ile-Ala-Gly-Gln-D-Arg-OH)

(1) Boc-Gln-Gly-OH

Boc-Gln-Gly-OBzl (3.1 g, 8 m mol) was deesterified in the manner similar to that of Example 2, paragraph 3).

Yield 2.0 g (83%)
m.p. 114°-116° C.
$[\alpha]_D^{20}$ −7.8° (C=0.7, DMF)

(2) Boc-Gln-Gly-Ile-Ala-Gly-Gln-D-Arg($NO_2$)-OBzl

Boc-Ile-Ala-Gly-Gln-D-Arg($NO_2$)-OBzl (3.2 g, 5 m mol) was demasked with respect to the N-masking group, and coupled with Boc-Gln-Gly-OH (1.7 g, 5.5 m mol) in the manner similar to that of Example 1, paragraph 7).

Yield 3.4 g (71%)
m.p. 235°-237.5° C. (decomp.)
$[\alpha]_D^{20}$ −13.5° (C=0.5, hexamethylphosphoryltriamide)

(3) DNP-Gln-Gly-Ile-Ala-Gly-Gln-D-Arg($NO_2$)-OBzl

Boc-Gln-Gly-Ile-Ala-Gly-Gln-D-Arg($NO_2$)-OBzl (1.2 g, 1.2 m mol) was demasked with respect to the N-masking group, and reacted with dinitrofluorobenzene (0.4 g, 2.2 m mol) in the manner similar to that of Example 1, paragraph 6).

Yield 900 mg (73%)

(4) DNP-Gln-Gly-Ile-Ala-Gly-Gln-D-Arg-OH)-OBzl

DNP-Gln-Gly-Ile-Ala-Gly-Gln-D-Arg($NO_2$)-OBzl (0.9 g, 0.9 m mol) was treated with hydrogen fluoride in the manner similar to that of Example 1, paragraph 8).

Yield 0.7 g (83%)
m.p. 210°-217° (decomp.)
$[\alpha]_D^{20}$ −10.8° (C=0.3, 50% acetic acid)
Elemental Analysis

|  | C | H | N % |
|---|---|---|---|
| Calcd. for $C_{35}H_{54}O_{14}N_{14}$ . $CH_3COOH$ . $H_2O$ | 45.67 | 6.22 | 20.16 |
| Found | 45.85 | 6.53 | 20.00 |

EXAMPLE 11

(DNP-Ala-Gly-Ile-Ala-Gly-Gln-D-Arg-OH)

(1) DNP-Ala-Gly-OH

Z-Ala-Gly-OH (1.5 g, 5.4 m mol) was demasked with hydrogen bromide in acetic acid in the manner similar to that of Example 1, paragraph 3) to yield precipitates.

The precipitates were reacted with dinitrofluorobenzene (1.2 g, 6.5 m mol) in the manner similar to that of Example 1, paragraph 6).

Yield 1.1 g (65%)
m.p. 170°-175° C. (decomp.)
$[\alpha]_D^{20}$ +78.9° (C=1.0, DMF)

(2) DNP-Ala-Gly-Ile-Ala-Gly-Gln-D-Arg($NO_2$)-OBzl

Boc-Ile-Ala-Gly-Gln-D-Arg($NO_2$)-OBzl (400 mg, 0.5 m mol) was demasked with respect to the N-masking group, and coupled with DNP-Ala-Gly-OH (160 mg, 0.5 m mol) in the manner similar to that of Example 1, paragraph 7).
Yield 290 mg (60%)
m.p. 219°–228° C. (decomp.)
$[\alpha]_D^{22}$ +39.4° (C=0.5, DMF)
(4) DNP-Ala-Gly-Ile-Ala-Gly-Gln-D-Arg-OH
DNP-Ala-Gly-Ile-Ala-Gly-Gln-D-Arg(NO$_2$)-OBzl (200 mg, 0.2 m mol) was treated with hydrogen fluoride in the manner similar to that of Example 1, paragraph 8).
Yield 150 mg (85%)
m.p. 214°–225° C. (decomp.)
$[\alpha]_D^{18}$ +35.5° (C=0.5, 50% acetic acid)

EXAMPLE 12.

DNP-Pro-Gln-Gly-Ile-Ala-Gly-Gln-D-Arg-OH.CH$_3$COOH.H$_2$O (4.96 mg) was neutralized with 0.1N sodium hydroxide, and dissolved in 0.05M tris-HCl buffer, pH 7.5, containing 0.15 M NaCl and 5 m MCaCl$_2$ to make 10 ml of the substrate solution (a) having a concentration of $5 \times 10^{-4}$ M. The substrate solution (b) was also prepared similarly by using DNP-Gln-Gly-Ile-Ala-Gly-Gln-D-Arg-OH.CH$_3$COOH.H$_2$O (4.48 mg).

0.9 ml Each of the substrate solutions was diluted with 0.88 ml of 0.05M tris-HCl buffer, pH 7.5, containing 0.15 M NaCl, and 5 m MCaCl$_2$. The resulting solution was mixed with 0.02 ml of purified collagenase, and incubated. 0.2 ml Aliquots of the reaction mixture were taken out at 0, 10, 20, 40, 60 and 120 minutes, and mixed with 0.5 ml of 1M hydrochloric acid for stopping the enzyme reaction.

The DNP-peptide fragments released were extracted by vigorous shaking with 1 ml of ethyl acetate-n-butanol (1:0.15, V/V) followed by centrifugation at 3,000–5,000 rpm and room temperature for 10 minutes to separate two layers completely. The degree of hydrolysis was determined by measuring the absorbance of the organic layer at 365 nm.

Result are shown in the following Table.

| Incubation time (min.) | Substrate solution(a) 00365 | Δ | Substrate solution(b) 00365 | Δ |
|---|---|---|---|---|
| 0 | 0.033 | — | 0.027 | — |
| 10 | 0.051 | 0.018 | 0.027 | 0 |
| 20 | 0.071 | 0.018 | 0.027 | 0 |
| 40 | 0.112 | 0.079 | 0.030 | 0.002 |
| 60 | 0.140 | 0.107 | 0.029 | 0.002 |
| 120 | 0.217 | 0.184 | 0.027 | 0 |

EXAMPLE 13.

1 ml of the substrate solution(a) prepared in Example 12 was mixed with 1.0 ml of non-specific peptidase, and the resulting solution was worked up as in Example 12. The results are shown in the following Table.

| Incubation time (min.) | 00365 | Δ |
|---|---|---|
| 0 | 0.053 | — |
| 10 | 0.054 | 0.001 |
| 20 | 0.056 | 0.002 |
| 40 | 0.058 | 0.004 |
| 60 | 0.060 | 0.007 |
| 120 | 0.063 | 0.010 |

EXAMPLE 14

0.2 ml Each of the substrate (solutions(a) and (b) prepared in Example 12 was mixed with 0.1 ml of synovial fluids from patients with osteoarthritis and rheumatoid arthritis, and incubated for 2 hours at 37° C. After stopping the enzyme reaction by adding 0.5 ml of 1 M hydrochloric acid, the DNP-peptide fragments released were extracted by vigorous shaking with 2 ml of ethyl acetate-n-butanol (1:0.15, V/V), and worked up as in Example 12 to obtain the collagenase activities.

Results are summarized in the following Table.

| | | Substrate solution(a) OD365/0.1 ml | | | Substrate solution(b) OD365/0.1 ml | | | Collagenase activity against | |
|---|---|---|---|---|---|---|---|---|---|
| | | | | | | | | Synthetic substrate | $^{14}$C-labeled[1] collagen |
| Case | Diagnosis | 0hr | 2hr | Δ | 0hr | 2hr | Δ' | (Δ-Δ'/ml . hr) | (units/ml) |
| S.N. | OA | 0.045 | 0.041 | 0 | 0.050 | 0.041 | 0 | 0 | 0.00 |
| M.M. | OA | 0.042 | 0.045 | 0.003 | 0.038 | 0.040 | 0.002 | neg[2] | 0.00 |
| S.O. | OA | 0.045 | 0.043 | 0 | 0.035 | 0.038 | 0.003 | 0 | 0.00 |
| M.T. | RA | 0.041 | 0.058 | 0.017 | 0.049 | 0.046 | 0 | 0.09 | 0.00 |
| M.N. | RA | 0.045 | 0.591 | 0.546 | 0.045 | 0.045 | 0.000 | 2.73 | 2.73 |
| T.O. | RA | 0.049 | 0.695 | 0.646 | 0.050 | 0.051 | 0.001 | 3.23 | 2.11 |

OA: osteoarthritis, RA: rheumatoidarthritis
[1] Collagenase activity was measured by using $^{14}$C-labeled reconstituted guinea pig skin collagen fibrils, as described in Biochim. Biophys. Acta. 263, 564(1972).
[2] Negligible within an error.

EXAMPLE 15.

Various DNP-peptide derivatives were dissolved in 0.05 M Tris-HCl buffer, pH 7.5, containing 0.15 M NaCl, 5 mM CaCl$_2$ and 0.02% bovine serum albumin to make a concentration of $5 \times 10^{-4}$ M. 0.1 ml Each of the peptide derivative solutions was mixed with an equal volume of purified collagenase (6.2 U/ml) or non-specific peptidases and incubated for various periods at 37° C. After stopping the enzyme reaction by adding 0.5 ml of 1 M HCl, the DNP-peptide fragments released were extracted by vigorous shaking with 1 ml of ethylacetate or ethyl acetate-n-butanol (1:0.15, V/V), and worked up as in Example 12.

Results are summarized in the following Table.

| DNP—peptide derivatives | Rate of hydrolysis** by | |
|---|---|---|
| | Collagenase (OD365/hr) | non-specific peptidases (OD365/hr) |
| DNP—Pro—Gln—Gly—Ile—Ala—Gly—Gln—D—Arg—OH* | 0.093 | 0 |
| DNP—Pro—Leu—Gly—Ile—Ala—Gly—Gln—D—Arg—OH | 0.276 | 0 |
| DNP—Pro—Gln—Gly—Ile—Ala—Gly—D—Arg—OH* | 0.157 | 0.021 |
| DNP—Pro—Gln—Gly—Leu—Ala—Gly—Gln—D—Arg—OH* | 0.243 | 0.031 |
| DNP—Pro—Ala—Gly—Leu—Ala—Gly—Gln—D—Arg—OH | 0.120 | 0.051 |
| DNP—Pro—Ala—Gly—Ile—Ala—Gly—Gln—D—Arg—OH | 0.070 | 0.010 |
| DNP—Gln—Gly—Ile—Ala—Gly—Gln—D—Arg—OH* | 0 | 0 |
| DNP—Ala—Gly—Ile—Ala—Gly—Gln—D—Arg—OH | 0 | 0.016 |

*DNP—peptide fragments released by enzyme were extracted with ethyl acetate-n-butanol (1:0.15, V/V).
**The average values of three experiments are shown.

EXAMPLE 16

NABS-Pro-Gln-Gly-Ile-Ala-Gly-Gln-D-Arg-OH was dissolved in 20% ethanol-0.05 M Tris-HCl buffer, pH 7.8, containing 0.15 M NaCl and 5 mM CaCl$_2$ to make a concentration of $5 \times 10^{-4}$ M. 0.5 ml of the solution was mixed with 0.1 ml of the purified collagenase (17.4 U/ml) and incubated for 60 minutes at 37° C. After stopping the enzyme reaction by adding 0.1 ml of 5 N-hydrochloric acid, the NABS-peptide fragments released were extracted with 1 ml ethyl acetate, followed by centrifugation at 3,000–5,000 rpm and room temperature for 10 minutes. The degree of hydrolysis was determined by measuring the absorbance of the organic layer at 389 nm.

OD389/hr/ml=0.100

EXAMPLE 17

PAS-Pro-Gln-Gly-Ile-Ala-Gly-Gln-D-Arg-OH was dissolved in 0.05 M Tris-HCl buffer, pH 7.8, containing 0.15 M NaCl and 5 mM CaCl$_2$ to make a concentration of $5 \times 10^{-4}$ M. 0.1 ml of the solution was mixed with 0.1 ml of the purified collagenase (17.4 U/ml) and incubated for 60 minutes at 37° C. After stopping the enzyme reaction by adding 0.5 ml of 1 N hydrochloric acid, the PAB-peptide fragments released were extracted with 1 ml ethyl acetate after saturated with sodium chloride, and worked up as in Example 16. The degree of hydrolysis was determined by measuring the absorbance of the organic layer at 325 nm.

OD325/hr/ml=1.117.

What is claimed is:

1. A method of measuring collagenase activity which comprises contacting a compound having the structure A-Pro-B-Gly-C-Ala-Gly-E with collagenase in an aqueous medium whereby said compound is hydrolyzed to release peptide fragments, extracting the released peptide fragments containing A with an organic solvent, and assaying the extract by subjecting the extract to colorimetry, said A being a hydrophobic, and neutral or acidic chromophore selected from the group consisting of 2,4-dinitrophenyl, 5-dimethyl-amino-1-naphthalene-sulfonyl, p-phenylazobenzyloxycarbonyl, p-nitrobenzyloxycarbonyl, p-(4-hydroxy-1-naphthylazo)-benzenesulfonyl and p-phenylazobenzoyl, said B being an amino acid residue of an alpha-amino acid having up to 15 carbon atoms occurring in protein, said C being Ile or Leu, said E being Gln-D-Arg-OH or D-Arg-OH, and all the amino acid residues except for Gly being L-configuration unless otherwise stated.

2. A method as set forth in claim 1, wherein said contacting is carried out at a temperature of 30° to 45° C. and at a pH of 6 to 9.

3. A method as set forth in claim 2, wherein said A is 2,4-dinitrophenyl, said B is a residue of a compound selected from the group consisting of alanine, leucine and glutamine, said C is Ile and said E is Gln-D-Arg-OH.

4. A method as set forth in claim 1 wherein said collagenase activity is calculated by subtracting from the absorbance obtained by said colorimetry the absorbance obtained by substituting said compound by A-B-Gly-C-Ala-Gly-E.

5. A method as set forth in claim 4, wherein said A is 2,4-dinitrophenyl, said B is Gln or Ala, said C is Ile and E is Gln-D-Arg-OH.

6. A method as set forth in claim 2, wherein said collagenase activity is calculated by subtracting from the absorbance obtained by said colorimetry the absorbance obtained by substituting said compound by A-B-Gly-C-Ala-Gly-E.

7. A method as set forth in claim 2, wherein A is a compound selected from the group consisting of 2,4-dinitrophenyl, p-(4-hydroxy-1-napthylazo)-benzenesulfonyl and p-phenylazobenzoyl.

8. A method as set forth in claim 1, wherein B is a residue of a compound selected from the group consisting of glycine, alanine, valine, leucine, serine, threonine, proline, phenylalanine, tyrosine, tryptophane, lysine, arginine, aspartic acid, asparagine, glutamic acid and glutamine.

9. A method as set forth in claim 1, wherein B is a residue of a compound selected from the group consisting of alanine, proline, leucine and glutamine.

* * * * *